United States Patent [19]

Fiore

[11] 4,384,470

[45] May 24, 1983

[54] METHOD AND APPARATUS FOR TESTING BLOOD VESSEL CATHETERS

[76] Inventor: Joseph Fiore, 508 E. 44th St., Kansas City, Mo. 64110

[21] Appl. No.: 253,799

[22] Filed: Apr. 13, 1981

[51] Int. Cl.³ .............................................. G01L 27/00
[52] U.S. Cl. ...................................... 73/4 R; 128/672
[58] Field of Search ......................... 73/4 R, 4 D, 168; 128/672, 673, 675

[56] References Cited

U.S. PATENT DOCUMENTS 4,261,208 4/1981 Hok et al. ............................ 128/674
4,328,698 5/1982 Bruton .................................. 73/4 R

OTHER PUBLICATIONS

Product Bulletin—"Swan-Ganz Flow-Directed Catheters".

"The Swan-Ganz Flow-Directed Thermodilution Catheter".

Primary Examiner—S. Clement Swisher
Attorney, Agent, or Firm—Kokjer, Kircher, Bradley, Wharton, Bowman & Johnson

[57] ABSTRACT

A method and device for testing the pressure readings obtained by a pressure sensing blood vessel catheter connected to a transducer and bedside monitor. The device includes a syringe which connects with a tube to provide an airtight test chamber. The pressure sensing end of the catheter can be inserted using sterile techniques into the test chamber through a tapered passage formed through a diaphragm on the end of the tube. A plunger can be extended into the syringe barrel to apply pressure to the test chamber. The pressure that it is applied to the catheter end is indicated on a calibrated scale imprinted on the syringe barrel for comparison with the pressure readings on the bedside monitor.

5 Claims, 2 Drawing Figures

U.S. Patent     May 24, 1983     4,384,470
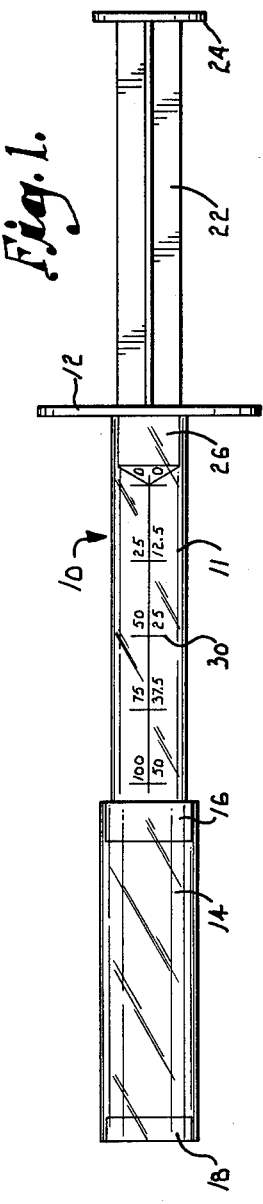
Fig. 1.
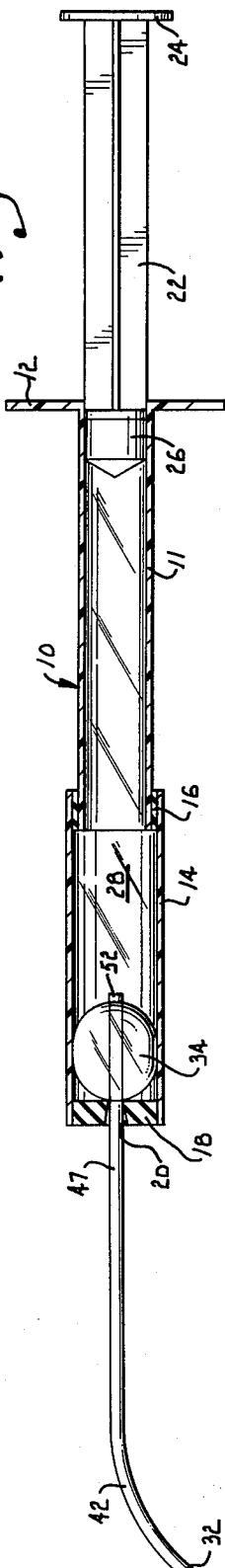
Fig. 2.
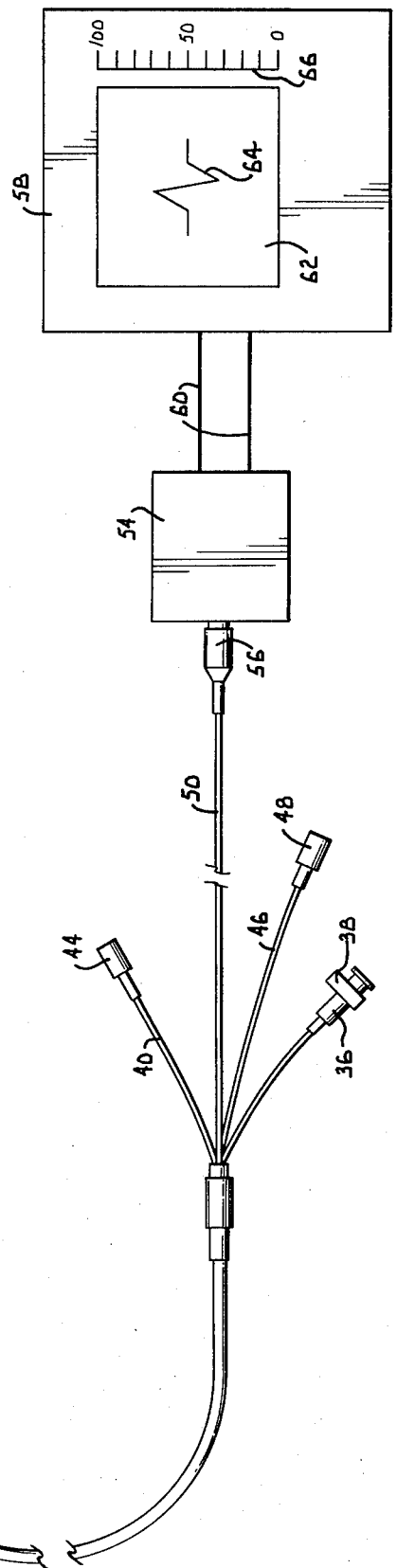

METHOD AND APPARATUS FOR TESTING BLOOD VESSEL CATHETERS

BACKGROUND AND SUMMARY OF THE INVENTION

This invention relates in general to testing apparatus and deals more particularly with a method and apparatus for pretesting of the accuracy of the pressure indications obtained from pressure sensing blood vessel catheters.

Blood vessel catheters have long been used for monitoring internal bodily pressures so that the patient can be treated appropriately based on the pressure readings. For example, balloon-tipped catheters are used by inserting them into a peripheral vein and threading them through the right ventricle of the heart. Once the pressure sensitive end of the catheter has been properly positioned in this manner, its opposite end is connected to a transducer which produces electrical signals based on the pressures sensed by the catheter. The transduced signals are applied to a bedside monitor which displays a waveform providing a visual representation of the pressures sensed by the catheter.

Although the catheters are manufactured under stringent quality control standards, the accuracy of the pressure indications depends also on accurate calibration of the transducer and on proper operation of the bedside monitor in combination with one particular catheter and one particular transducer. Thus, if the transducer is calibrated inaccurately, as sometimes occurs, or if the overall combination is lacking in accuracy, the pressure readings will not be correct even if the catheter itself is of the highest quality. In the past, there has been no effective technique available for checking the accuracy of the overall assembly of components, and the inaccurate pressure readings that sometimes occur can lead to inappropriate treatment and other adverse consequences.

The present invention is directed to a method and apparatus for independently confirming the accuracy of a pressure sensing blood vessel catheter, as used in combination with a particular transducer and monitoring instrument, prior to insertion of the catheter into the body. In accordance with the invention, a testing syringe and plastic tube cooperate to provide an airtight test chamber. The syringe and tube are sterile and are equipped with a diaphragm through which the pressure sensitive end of the catheter can be extended into the test chamber. A plunger can be extended into the opposite end of the syringe barrel to apply pressure to the pressure sensitive end of the catheter. A calibrated scale imprinted on the syringe barrel gives an accurate pressure reading that can be compared with the pressure reading of the bedside monitor in order to asertain the accuracy of the assembly of pressure sensing equipment.

DETAILED DESCRIPTION OF THE INVENTION

In the accompanying drawing which forms a part of the specification and is to be read in conjunction therewith and in which like reference numerals are used to indicate like parts in the various views:

FIG. 1 is a side elevational view of a testing device constructed according to a preferred embodiment of the present invention, with the plunger in a retracted position; and FIG. 2 is a sectional view of the test device in use to test the accuracy of the pressure readings obtained from a balloon tipped blood vessel catheter.

Referring now to the drawing in more detail, numeral 10 designates a syringe having a cylindrical barrel 11 and an enlarged flange 12 on one end. The end of the syringe barrel opposite flange 12 is open and is received in the open end of a plastic tube 14. A seal ring 16 provides a seal between the ends of the syringe barrel and tube. A rubber diaphragm 18 is secured in the end of tube 14 opposite the end which receives syringe barrel 11. A passage 20 is formed centrally through diaphragm 18 and is tapered from the outside surface of the diaphragm to the inside surface thereof. The passage is tapered so that an airtight seal is created when a pressure sensitive catheter is inserted through it. The syringe 10 and tube 14 are sterile and are formed of a transparent material.

The syringe barrel 11 receives a plunger 22 having a ribbed body and a circular flange 24 on one end. The opposite end of the plunger carries a piston 26 having a conical tip. Piston 26 fits closely within the syringe barrel and seals against the barrel in airtight fashion. Consequently, when plunger 22 is extended into syringe barrel 11, the pressure builds up within the test chamber 28 presented within syringe barrel 11 and tube 14. The pressure build up is directly proportional to the distance piston 26 is extended into the test chamber. Plunger 22 is sterile.

A numerical scale 30 is imprinted on the barrel of syringe 10 and is calibrated to provide pressure readings representive of the pressures applied to the test chamber 28. The scale includes an upper set of numerals which correspond to pressure readings (in millimeters of mercury) and a lower set of numerals which correspond to the number of millimeters the plunger is extended into the syringe. For example, when the plunger is extended into the syringe barrel such that the conical tip of piston 26 is aligned with the calibration mark labeled "75", the pressure within the test chamber is 75 mm Hg. The corresponding distance reading is "37.5" to indicate that plunger 22 has been extended into the syringe barrel 37.5 millimeters from the "zero" or start position. The actual pressure scale will depend on the internal volume of the testing chamber.

The testing device is used to test the accuracy of pressure sensing blood vessel catheters such as the balloon tipped catheter 32 shown in FIG. 2. Catheter 32 is a flow-directed thermal dilution catheter of the type commercially available under the trademark "Swan-Ganz". Catheter 32 includes four lumens, one of which terminates at an inflatable balloon 34 located near the distal end of the catheter tube. The balloon 34 can be inflated through a fitting 36 which is equipped with a sliding gate valve 38. Another lumen 40 terminates in an injection port 42 located approximately 30 centimeters from the catheter tip. Injectate necessary for cardiac output computation can be injected into a fitting 44, through lumen 40 and into the right atrium through the injection port 42. Another lumen 46 contains the electrical leads for a thermistor 47 and connects to a thermistor fitting 48. The final lumen 50 senses internal bodily pressures such as chamber pressures, pulmonary artery pressure, and pulmonary capillary wedge pressure. Lumen 50 terminates in a pressure sensitive tip 52 on the distal end of the catheters located adjacent to the balloon 34.

The pressure sensing lumen 50 can be connected to a transducer 54 by means of a fitting 56 carried on the end of lumen 50. Transducer 54 receives the internal bodily pressure sensed by tip 52 and produces electrical signals proportional to the sensed pressures. The signals are applied to a bedside monitor 58 which can be connected with the transducer by electrical lines 60. The bedside monitor 58 has a screen 62 which displays a waveform 64 representative of the pressures sensed by the pressure sensing lumen 50. A calibrated scale 66 is provided beside screen 62 to give the pressure readouts in mm Hg.

The testing device permits pretesting of the combination catheter 32, transducer 54 and bedside monitor 58 prior to insertion of the catheter into the body. Even if the catheter is of the highest quality, the particular transducer with which it is used may be calibrated inaccurately, the bedside monitor 58 may be lacking in reliability, or the overall assembly of components may for some other reason give inaccurate pressure indications. In order to prevent inaccurate pressure readings and possible inappropriate therapy based thereon, it is desirable to independently confirm the accuracy of the combination of components before insertion of the catheter into a blood vessel.

In accordance with the invention, the pressure indications provided by the catheter are tested by inserting the pressure sensitive tip 52 through the passage 20 of diaphragm 18 and into the testing chamber 28. The balloon 34 can then be inflated through fitting 36 until it fits rather snugly against the internal wall of tube 14 adjacent diaphragm 18. The tapered configuration of passage 20 assures that catheter 32 will seal effectively with the diaphragm to prevent air leakage.

Fitting 56 is connected to transducer 54, and the transducer is connected to bedside monitor 58. Once this has been done, plunger 22 is extended into the syringe barrel 10 in order to build up pressure in the test chamber 28. The pressure indications on scale 30 are then compared with the pressure indications provided on the monitoring instrument 58 in order to confirm the accuracy of the catheter, transducer and bedside monitor in combination. For example, if plunger 22 is extended until the tip of piston 26 is aligned with the "50 mm Hg" calibration mark on scale 30, the waveform 64 should provide a reading of "50 mm Hg" on scale 66. If it does not, this particular combination of components should not be used to obtain internal bodily pressure indications because the pressure indications are inaccurate.

As previously indicated, the syringe 10, tube 14 and plunger 22 are sterile. It is contemplated that the test device will be maintained in a sterilized container until use, and that sterile techniques will be used to insert the distal tip of the catheter into the test chamber 28. Sterile techniques need not be used in connecting the proximal end of the catheter to transducer 54.

Although use of the testing device has been described in connection with testing a "Swan-Ganz" balloon tipped catheter, it is equally useful for the testing of other types of pressure sensing blood vessel catheters. It is preferred that plunger 22 to be extended into barrel 11 through its entire range and that the waveform 64 be monitored continuously in order to ascertain the accuracy of the readings throughout the range of the instrument. The scale 30 on the syringe barrel should be calibrated up to about 200 mm Hg if the device is to be used to test catheters that are inserted into arterial vessels, while the scale on the syringe should be incremented up to about 50 mm Hg if the catheter is used to provide venous pressure readings.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative and not in a limiting sense.

Having thus described the invention, I claim:

1. A device for testing the accuracy of pressure indications given by a transducer device in response to pressure exerted on a pressure sensitive end portion of a blood vessel catheter, said device comprising:

a hollow tube presenting a fluid tight test chamber therein adapted to receive said pressure sensitive end portion of the catheter;

a diaphragm on one end of said tube having a passage therein sized to closely receive said end portion of the catheter in a manner to effect a seal between the diaphragm and catheter, said passage being tapered from the outside surface of the diaphragm to the inside surface thereof;

a plunger carrying a piston which is received in said tube in sealing relation therewith, thereby building up pressure in said test chamber in proportion to movement of said plunger into the test chamber toward said pressure sensitive end portion of the catheter; and a scale on said tube calibrated to cooperate with said plunger in a manner to provide an indication of the pressure in said test chamber, whereby the plunger can be extended into said tube and the pressure indication on said scale can be compared with the pressure indication provided by the transducer device to ascertain the accuracy of the transducer device indications prior to insertion of the catheter into the blood vessels.

2. A device as set forth in claim 1, wherein said tube and plunger are sterile.

3. A device for testing the accuracy of pressure indications provided by a pressure sensing blood vessel catheter in combination with a transducer and a visual display device, said device comprising:

a sterile tube having a diaphragm on one end thereof presenting a passage adapted to receive a pressure sensitive lumen of the catheter in extension through said passage and into the tube, said passage being sized to permit the diaphragm to seal against the catheter and being tapered from the outside surface of the diaphragm to the inside surface thereof;

a sterile syringe barrel extending into the opposite end of said tube and cooperating with said tube to present a fluid tight test chamber;

a sterile plunger carrying a piston in sealing contact with the internal wall of said syringe barrel, said plunger being capable of extension into said test chamber to build up pressure therein in proportion to the extension of said piston into the chamber; and a scale on said syringe barrel calibrated to cooperate with said plunger to provide an indication of the pressure in said chamber, whereby the accuracy of the catheter, transducer and display device can be confirmed by comparing the pressure indications on the scale and display device prior to insertion of the catheter into the blood vessels.

4. A device as set forth in claim 3, wherein the catheter has an inflatable balloon thereon adjacent the end of said pressure sensitive lumen, said balloon being inflatable within said tube at a location to seal against said diaphragm upon extension of said plunger into the test chamber.

5. A device for testing the accuracy of pressure indications provided by a pressure sensing blood vessel catheter in combination with a transducer and a visual display device, said device comprising:

a sterile tube having a diaphragm on one end thereof presenting a passage adapted to receive a pressure sensitive lumen of the catheter in extension through said passage and into the tube, said passage being sized to permit the diaphragm to seal against the catheter and said catheter having an inflatable balloon thereon adjacent the pressure sensitive lumen;

a sterile syringe barrel extending into the opposite end of said tube and cooperating with said tube to present a fluid tight test chamber;

a sterile plunger carrying a piston in sealing contact with the internal wall of said syringe barrel, said plunger being capable of extension into said test chamber to build up pressure therein in proportion to the extension of said piston into the chamber and said balloon being inflatable within said tube at a location to seal against said diaphragm upon extension of said plunger into the test chamber; and a scale on said syringe barrel calibrated to cooperate with said plunger to provide an indication of the pressure in said chamber, whereby the accuracy of the catheter, transducer and display device can be confirmed by comparing the pressure indications on the scale and display device prior to insertion of the catheter into the blood vessels.

* * * * *